(12) United States Patent
Harkins

(10) Patent No.: US 8,881,733 B1
(45) Date of Patent: Nov. 11, 2014

(54) MANDIBULAR ADVANCEMENT DEVICE

(76) Inventor: Stephen J. Harkins, Tucson, AZ (US)

( * ) Notice: Subject to any disclaimer, the term of this patent is extended or adjusted under 35 U.S.C. 154(b) by 264 days.

(21) Appl. No.: 13/468,766

(22) Filed: May 10, 2012

Related U.S. Application Data

(60) Provisional application No. 61/487,588, filed on May 18, 2011.

(51) Int. Cl.
*A61F 5/56* (2006.01)
*A61C 5/14* (2006.01)

(52) U.S. Cl.
USPC .......................... 128/848; 128/860; 128/861

(58) Field of Classification Search
CPC ............. A61F 5/56; A61F 5/566; A61C 5/14; A61C 7/08; A63B 71/085
USPC ........... 128/848, 859–862; 602/902; 433/6, 7, 433/19, 37, 140, 93
See application file for complete search history.

(56) References Cited

U.S. PATENT DOCUMENTS

| | | |
|---|---|---|
| 6,604,527 B1 | 8/2003 | Palmisano .................... 128/848 |
| 6,983,752 B2 | 1/2006 | Garabadian ................... 128/848 |
| 7,451,767 B2 | 11/2008 | Keropian | 
| 7,637,262 B2 | 12/2009 | Bailey .......................... 128/848 |
| 2009/0178684 A1* | 7/2009 | Greenburg .................... 128/848 |
| 2010/0043805 A1* | 2/2010 | Kelly ............................ 128/848 |
| 2011/0220125 A1* | 9/2011 | Van Dyke et al. ............ 128/848 |

OTHER PUBLICATIONS

Davis Dental Laboratory brochure (2 pgs).
SomnoDent MAS Product Guide, downloaded from www.somnomed.com on Oct. 13, 2010 (4 pgs).

* cited by examiner

*Primary Examiner* — Patricia Bianco
*Assistant Examiner* — Kari Petrik
(74) *Attorney, Agent, or Firm* — Hayes Soloway P.C.

(57) ABSTRACT

A mandibular advancement device used in the management of snoring, obstructive sleep apnea, TMD and bruxism, comprises a maxillary tray for receiving/retaining maxillary teeth, a mandibular tray for receiving/retaining mandibular teeth, and at least two advancement members/prongs located on the mandibular tray at the anterior-lateral regions thereof. The advancement members/prongs, when in use, contact the outer surface of the maxillary tray in an anterior-lateral region thereof, thereby advancing/retaining the mandible and tongue in a protrusive position. Raised occlusal surfaces/bite pads in a region contiguous and posterior to the advancement prongs allow a passive tongue retaining gap or space to be formed in the anterior and posterior regions of the device. A lingual retaining strap may be provided between opposite posterior portions of the mandibular tray to passively retain the tongue in a protruded, non-obstructive position.

16 Claims, 4 Drawing Sheets

MANDIBULAR ADVANCEMENT DEVICE

CROSS REFERENCE TO RELATED APPLICATION

This application claims priority from U.S. Provisional Application Ser. No. 61/487,588, filed May 18, 2011, the entire disclosure of which is incorporated herein by reference.

FIELD OF THE INVENTION

The present invention relates to a mandibular advancement device, in particular, a mandibular advancement device that is simpler in design than those known in the field, and that is capable of retaining the tongue in a non-obstructive position. The invention has particular utility for treating and alleviating symptoms associated with snoring, obstructive sleep apnea, bruxism and tempromandibular joint disorders, and will be described in connection with such utility, although other utilities are contemplated.

BACKGROUND OF THE INVENTION

It is well known that snoring and obstructive sleep apnea are typically caused by a partial or complete obstruction of the pharyngeal airway during sleep. Mandibular advancement devices advance the mandible forward and consequently reduce the likelihood of the tongue restricting the airway.

A number of mandibular advancement oral appliances have been proposed in the prior art. For example, U.S. Pat. No. 6,983,752, issued to Garabadian, discloses a mandibular advancement device that includes bite pads on maxillary and mandibular trays. The bite pads are located in a posterior portion of the device. The bite pads on the mandibular tray are located anterior to the bite pads of the maxillary tray. As such, when the user bites down, the mandible is extended outward due to the placement of the bite pads. That is, the anterior bite pads on the mandibular tray are held forward by the contact with the posterior bite pads on the maxillary tray. This device thus requires bite pads on both the mandibular and the maxillary trays in order to advance the mandible to the desired position.

U.S. Pat. No. 7,637,262 to Bailey discloses an oral appliance having features similar to those disclosed by Garabadian, and further includes the feature that the bite pads may form a guide plane for advancing the mandibular tray along the guide plane upon vertical closure between the trays.

Similarly, U.S. Pat. No. 6,604,527 to Palmisano discloses a mandibular advancement device that requires engaging members on both the mandibular and maxillary trays to advance the mandible. Palmisano's device includes lower flanges on a lower plate which have a trailing edge that engages with a leading edge of an upper flange that is disposed on an upper plate. The flanges are all located in a posterior portion of the device. The positioning of the flanges causes the mandible to be advanced when the device is used.

Because the Garabadian, Bailey and Palmisano devices require engaging members (e.g., bite pads, flanges, etc.) on both an upper and a lower tray, the devices can be cumbersome and awkward for a patient to wear, particularly for a full night's sleep and may cause dental/muscle/TMJ pain if the patient bruxes/clenches the teeth. Moreover, the fact that at least four engaging members are required in these devices increases the complexity of the device and increases the likelihood of failure of the device due to the failure of any individual engaging member. If the patient's mouth drops open during sleep, especially in the deeper stages of sleep (stages N3 and REM), the bite pads or guide members can disengage and allow the mandible and tongue to fall back into the oropharynx, obstructing the airway.

U.S. Pat. No. 7,451,767 to Keropian discloses an oral appliance that includes a "transpalatal bar" which extends across the posterior region of the appliance and acts as a tongue depressor to open the air passage. Posterior projections/extensions may be formed on the transpalatal bar, which hold the tongue down even further to further open the airway. However, Keropian's "transpalatal bar" is located on the underside of the appliance which is fitted to the palate and covers the upper teeth. Thus, the bar is located no lower (lingual side) than the occlusal surface of the posterior maxillary teeth. As such, the extent of tongue depression provided by the transpalatal bar is limited and can create problems if extended further down into the oropharynx. There is a problem with this design activating the gag reflex, which may not be well tolerated by many patients. This prior art appliance requires multiple follow up office visits to extend the "transpalatal bar" down the posterior aspect of the tongue to hold it forward. Regurgitation of stomach acid/digestive enzymes is also a problem while sleeping as this design does not allow the patient to swallow normally, preventing the tongue from creating a pharyngeal seal, resulting in a "reverse swallow" when in the mouth. This results in a negative esophageal pressure (partial vacuum) to develop in the esophagus and pharynx, causing the gastric contents to be "sucked up" from the stomach into the esophagus, pharynx, oral, nasal, and sinus cavities. This could be described as a form of "Iatrogenic" Gastric Esophageal Reflux Disorder (GERD), which has significant morbidity and even mortality as a long-term outcome.

Thus, there is a need in the field for a mandibular advancement oral appliance that can treat or alleviate symptoms caused by snoring and obstructive sleep apnea by advancing the mandible with a simpler device that requires fewer engagement members than required in the prior art. Furthermore, there is a need in the field for an oral appliance that can advance the mandible and retain the patient's tongue in a non-obstructive forward position when the tongue and pharyngeal muscle relax during the deepest stages of sleep, without significant side effects such as GERD.

SUMMARY OF THE INVENTION

The present disclosure is directed to a mandibular advancement device that overcomes the aforesaid and other disadvantages of the prior art. More particularly, the present disclosure provides a mandibular advancement device that includes a maxillary tray and a mandibular tray, and the mandibular tray has at least two advancement members that, when in use, protrude over an outer surface of the maxillary tray, thereby advancing the user's mandible and opening the airway.

In one aspect, the present disclosure provides a mandibular advancement device that includes a maxillary tray for receiving maxillary teeth, a mandibular tray for receiving mandibular teeth, and at least two advancement members/prongs located on the mandibular tray in an anterior region thereof. The advancement members/prongs, when in use, contact the outer surface of the maxillary tray in an anterior region thereof, thereby advancing and retaining the mandible. The advancement members/prongs can be modified to further protrude or retrude the mandible by adding or subtracting orthodontic acrylic from the articulating surfaces (posterior surface of the advancement members/prongs on the mandibular appliance and/or the anterior surface of the maxillary appliance). Cold cure or light activated orthodontic acrylic can be utilized for this purpose. The advancement members/prongs may be fabricated from thermoplastic dental/orthodontic hard acrylic, plastics, thermaplastics or other polymeric material. The advancement prongs can also be fabricated from stainless steel dental/orthodontic wire (0.035-0.040 inch diameter) which is bent into an elliptical shaped loop and bonded to the anterior flange of the mandibular tray with orthodontic acrylic. The preferred material is a dental/orthodontic hard acrylic. When heated (e.g., a small alcohol torch), the members/prongs may be reshaped (tipped forward or backward) in the lab. After air cooling, the advancement members/prongs harden and will then hold the mandible in the more protruded or retruded position. If orthodontic wire is used to fabricate the advancement members/prongs, the members/prongs can be bent backward or forward to further protrude or retrude the mandible when the members/prongs contact the anterior flange of the maxillary tray in the mouth. The addition or reduction of acrylic from the anterior flange of the maxillay tray or tipping/reshaping of the advancement prongs allows titration of the appliances in the anterior-posterior dimension.

The mandibular tray includes two or more raised occlusal surfaces (vertical opening pads) in a region posterior to the advancement members, allowing a gap or open space to be created large enough for a user's tongue to remain forward, when in use, between the advancement members/prongs in the most anterior region of the device and posterior of the members/prongs to prevent the tongue from being forced back, into the pharynx when the jaw is closed during sleep.

The advancement members/prongs are attached/bonded to the mandibular tray at a region ranging from the distal aspect of the user's mandibular canines, posterior to the distal aspects of the second premolars when in use. The exact location of the advancement members/prongs within this range would depend on the size of the tongue and the amount of mandibular anterior repositioning desired.

The maxillary tray and the mandibular tray should be precisely fabricated molded to conform to a user's teeth and soft tissues with no pressure or discomfort.

In a further aspect, a flexible (elastic) strap may be disposed between the two posterior aspects (right and left sides) of the mandibular tray, and the strap should be configured to lie passively over the superior posterior (dorsal) surface of a user's tongue when in use.

The lingual strap should include a 3-5 mm thick pad, fabricated from orthodontic soft bit guard material coupled to a length of orthodontic elastic power chain or dental wire that is connected between the two sides of the most posterior aspects of the mandibular tray.

Accordingly, an advantage of the present disclosure is to provide a mandibular advancement device that can treat or alleviate symptoms caused by snoring and obstructive sleep apnea by advancing the mandible and opening the vertical space between the dental arches during sleep with a simpler device that requires fewer engagement members than required in the prior art. The advancement members/prongs, attached to the anteriolateral aspects of the mandibular tray, should be long enough vertically to hold the mandible and tongue in the desired anterior position, maintaining a patent oropharyngeal airway, even if the mouth drops open during the deeper stages of sleep or if the user is "mouth breathing". Furthermore, an advantage of the present disclosure is to provide a tongue retainer to further hold the tongue in a less obstructive protruded position and prevent it from falling back, blocking the airway during sleep, without creating a reverse swallow and GERD.

The features, functions and advantages that have been discussed can be achieved independently in various embodiments of the present disclosure or may be combined in yet other embodiments, further details of which can be seen with reference to the following descriptions and drawings.

BRIEF DESCRIPTION OF THE DRAWINGS

Further features and advantages of the invention will be seen from the following detailed description, taken in conjunction with the accompanying drawings, wherein like numerals depict like parts, and wherein.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

In a normal bite position, the mandibular teeth are generally located slightly posterior to the corresponding maxillary teeth. In particular, the mandibular central incisors are normally located slightly posterior to the maxillary central incisors. For mandibular advancement, it is generally desirable to advance the mandible, i.e. protrude/extend the mandible outward, preferably 50-70% of maximum mandibular protrusion. The mandibular incisors would then be advanced anterior to the maxillary incisors.

Figure 1:
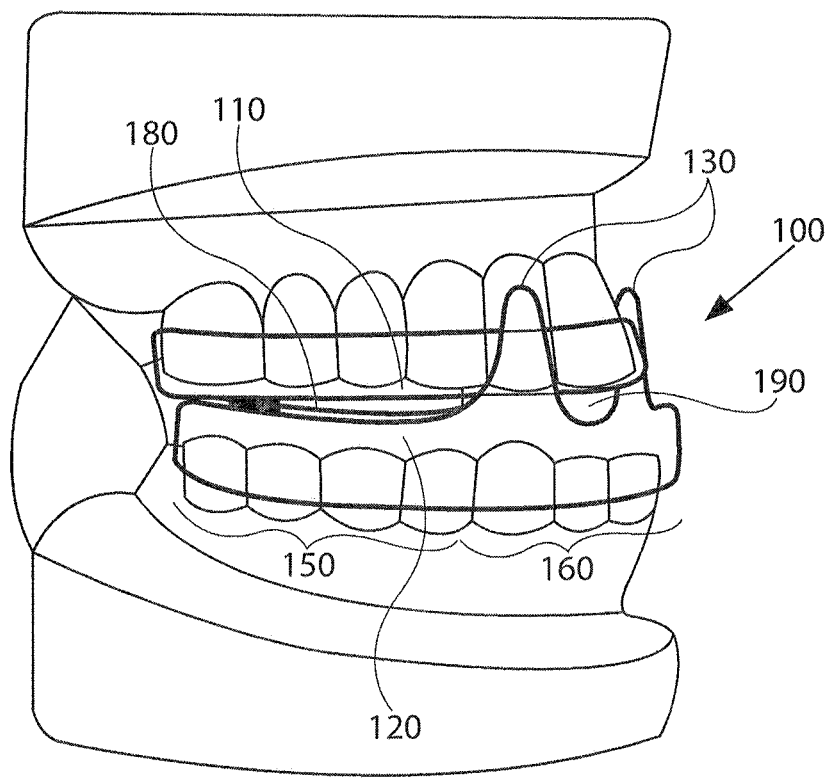
FIG. 1 illustrates a mandibular advancement device in accordance with an embodiment of the present disclosure.

FIG. 1 schematically illustrates a primary example of a mandibular advancement device provided by the present disclosure. The device 100 includes a maxillary tray 110 adapted for receiving and retaining a user's maxillary teeth, and a mandibular tray 120 for receiving and retaining the mandibular teeth. The maxillary tray 110 fits over all of the maxillary teeth of a user, while the mandibular tray 120 fits over all of the mandibular teeth of a user. The maxillary tray 110 and the mandibular tray 120 both have an anterior portion 160 which receives the anterior teeth of the user, and a posterior portion 150 which receives the posterior teeth.

The trays 110, 120 can be formed from orthodontic materials such as, for example, cold or heat cure acrylic, plastics, thermoplastics or other such polymeric material, or any other acceptable materials. The maxillary tray 110 and mandibular tray 120 preferably are custom fabricated to conform to a patient's teeth. The trays 110, 120 may be fitted to conform to the user's teeth by known manual monomer-polymer mixing/molding, heat molding and/or injection molding techniques. In one embodiment, the trays 110, 120 are of the "vaccuform" variety, i.e. the trays are made of a thermosoftening material such as a vinyl orthodontic acrylic which softens when heated. As such, the trays 110, 120 may be heated and pressure molded over the patient's plaster dental casts, thereby custom molding the trays 110, 120 to the shape of his/her maxillary and mandibular dentitions.

The mandibular tray 120 includes two advancement members or prongs 130 that protrude upward from an anterior portion 160 of the mandibular teeth. Preferably, the advancement prongs 130 protrude upward from a region between about the distal aspect of the mandibular canines to about the distal aspect of the mandibular first premolars. More preferably, the advancement members/prongs 130 protrude upward from the distal aspect of the mandibular canine-premolar region.

When placed in a person's mouth, the advancement members/prongs 130 on the mandibular tray 120 protrude upward such that the posterior surface of the prongs 130 contacts an outer anterior surface of the maxillary tray 110 in an anterior region 160, e.g., over about the mesial aspect of the maxillary canines to the distal aspect of the maxillary premolars when the person closes his/her mouth. The resulting contact between the protruding members 130 on the mandibular tray 120 and the outer surface of the maxillary tray 110 positions and retains the mandible in an outwardly extended/protruded position, thereby causing the airway to open and to remain open/forward.

The mandibular tray 120 has raised occlusal surfaces (pads) 180 in a region posterior to the advancement members/prongs 130. The raised occlusal pads prevent the maxilla and mandible from overclosing, increasing the volume of the oral and pharyngeal cavities. The vertical occlusal pads can be increased or decreased in height as indicated to further increase the airway space. The occlusal pads can be modified to intentionally alter the position of the TMJ condyles (balls) within the fossae (sockets), reducing mechanical loading (compression) inside the TMJs if the patient is a jaw clencher/bruxer. The occlusal pads also prevent the muscles of mastication from overclosing, preventing jaw muscle pain. When the raised occlusal pads are optimally established, TMD and jaw muscle symptoms are significantly reduced and in most cases eliminated. Thus, when the user positions the maxillary tray 110 and mandibular tray 120 over the maxillary and mandibular dentitions, respectively, and closes/bites down, the raised surface (vertical bite pads) 180 in the region posterior to the protruding members 130 of the mandibular tray occludes with the corresponding region of the maxillary tray 110. A lingual or tongue space 190, i.e. a gap of empty space, is formed in the region between the protruding members 130. The lingual space 190 provides space for the user to passively retain his/her tongue, thereby further allowing the user's tongue to position forward and anterior to the pharyngeal airway. If this tongue space is not maintained when the jaw is closed during sleep, the tongue will be forced back, into the pharyngeal airway space, producing airway obstruction.

Figure 2:
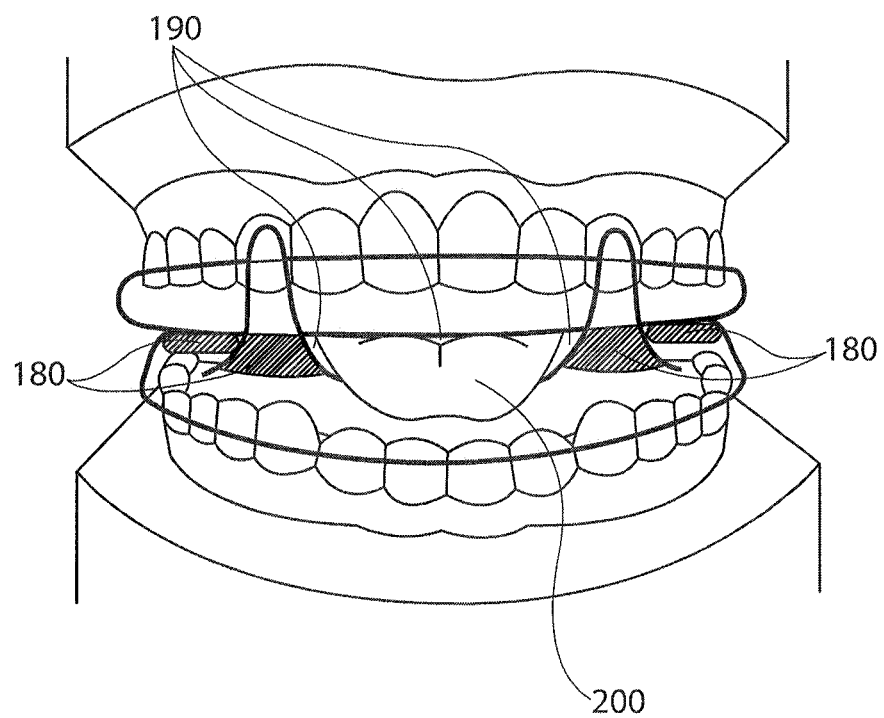
FIG. 2 illustrates a front view of the mandibular advancement device of FIG. 1.

As can be seen from a front view of the mandibular advancement device, illustrated by FIG. 2, the tongue 200 may be extended as the wearer closes/bites down, and the tongue will fit in the space provided by the lingual space 190. With the tongue so positioned, the tongue can be retained in the lingual space 190 and passively held forward of the pharyngeal airway during sleep.

Figure 3A:
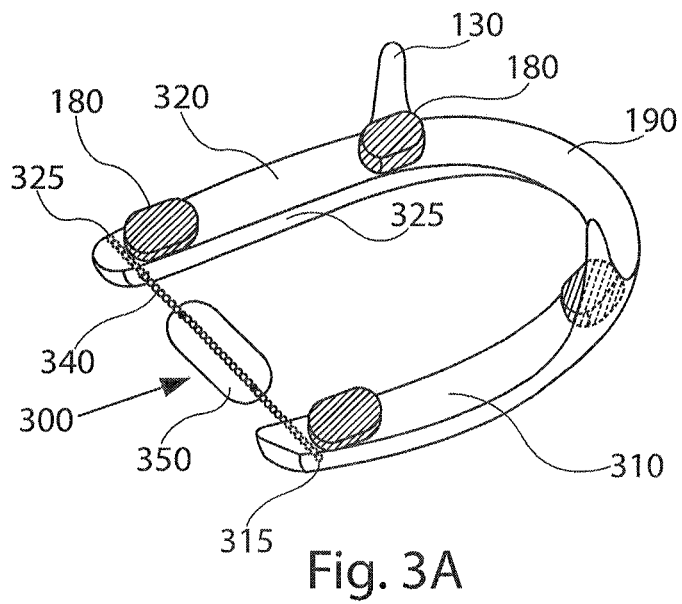
FIGS. 3A and 3B illustrates a mandibular advancement device in accordance with yet other alternative designs of a mandibular advancement (wire loop advancement prongs) in accordance with the present disclosure.

In one embodiment shown in FIG. 3A, a lingual strap 300 may be provided with the mandibular advancement device 100. The lingual strap 300 is disposed between the right and left posterior portions 310, 320 of the mandibular tray 120. For example, the lingual strap 300 may be connected between the buccal (outside) surface 315 of the mandibular tray and the contralateral buccal surface 325 of the mandibular tray. In use, the lingual strap 300 is placed over the superior posterior (dorsal) surface of the patient's tongue, thereby further holding/retaining the tongue in place or forward and reducing or preventing pharyngeal airway obstruction related to the tongue falling back during deep sleep. The lingual strap 300 may be composed of any suitable materials. For example, the lingual strap 300 may be made of elastic orthodontic power chain 340, or flexible orthodontic/dental wire 340A (FIGS. 4A and 4B, described below), attaching to the posterior sides of the mandibular tray on the buccal flange in the second molar area, and a different orthodontic material (3-5 mm thick flexible bite guard material) 350, which forms a retention pad for the tongue, connected to the power chain 340 or orthodontic/dental wire 340A for contacting the superior posterior (dorsal) surface of the tongue, retaining the tongue in a more forward, protruded position when it relaxes. The underside of the tongue retaining pad may be irregular or rough to increase the retention of the tongue. Biocompatible or dental/denture adhesives can also be applied to the tongue side of the tongue retention pad to further increase tongue retention.

Figure 3B:
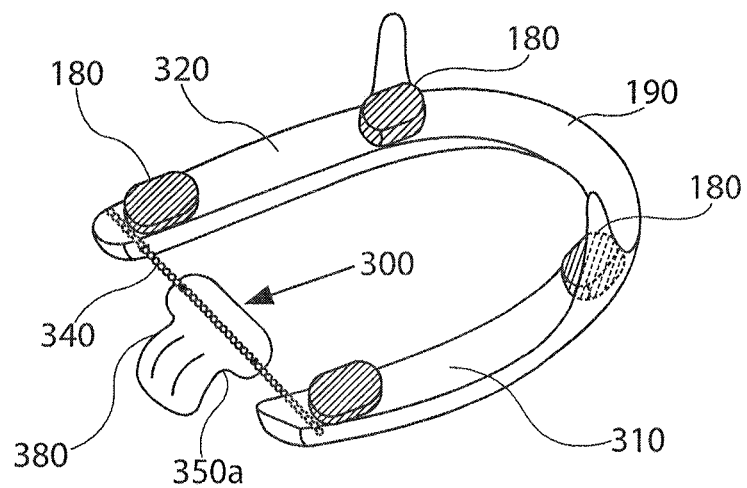

In yet another embodiment, shown in FIG. 3B, a downwardly curved extension 380 is provided on the tongue retaining pad 350a for engaging with the distal end of the wearer's tongue. The tongue must be allowed to seal off the pharyngeo-velopharynx when the patient swallows during sleep. The orthodontic power chain material or orthodontic/dental wire used to hold the tongue retention pad must be elastic and/or flexible enough to allow the dorsal aspect of the tongue to position up and back during swallowing, preventing choking or drooling from saliva buildup, and/or gastric regurgitation (GERD).

Figure 4A:
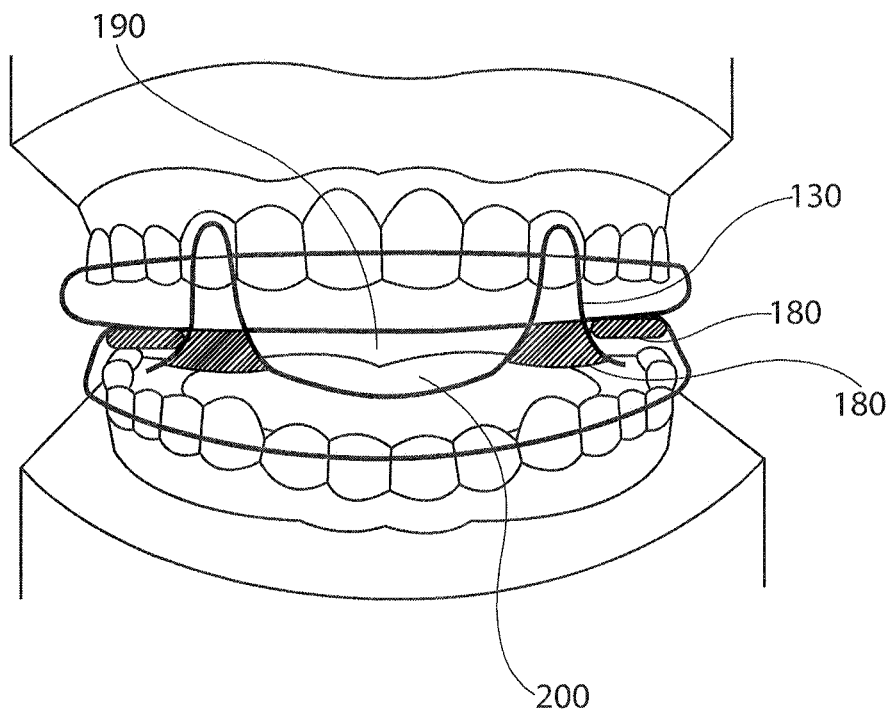
FIGS. 4A and 4B is a view similar to FIGS. 2 and 3B, respectively, of a mandibular advancement device in accordance with yet a further embodiment of the present disclosure.
Figure 4B:
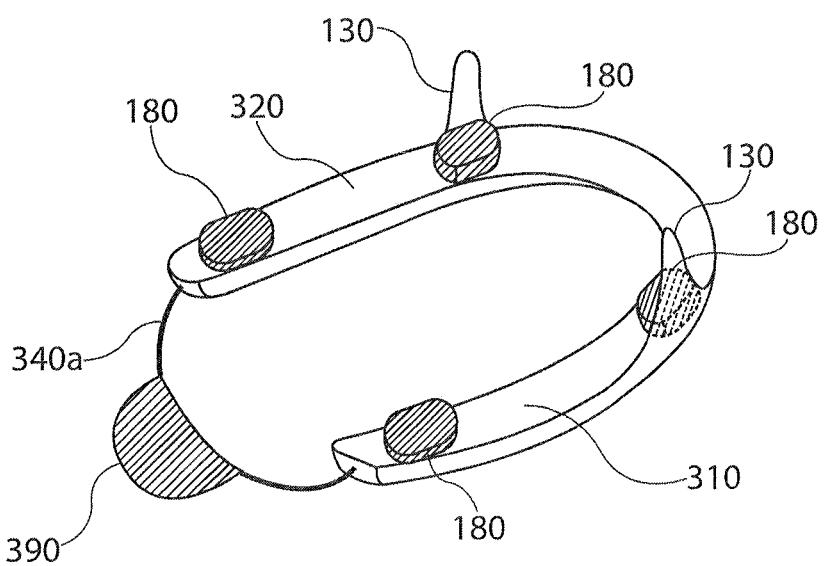

In yet another embodiment, illustrated in FIGS. 4A and 4B, the lingual strap is formed of flexible orthodontic/dental wire 340A. A downwardly curved extension 390, similar to extension 380 shown in FIG. 3B, is provided for engaging with the distal end of the wearer's tongue.

Heat cure, cold cure or UV light activated orthodontic/dental acrylic can be added to or removed from the articulating surfaces of the maxillary or mandibular trays by the dentist or dental technician on follow up visits to titrate the appliance (further protrude/retrude, increase or decrease the vertical dimension of the mandibular tray) as indicated.

The mandibular advancement device provided by the present disclosure, by causing the mandible to be protruded and separated vertically from the maxilla, allows the tongue to remain forward/protruded during sleep, preventing it from being forced back or collapsing back into the airway, and thereby holding open the pharyngeal airway during sleep. This prevents snoring and obstructive sleep apnea. Because the tongue is attached to the mandible along the floor of the mouth, retaining the mandible forward and more open, will simultaneously retain the tongue in a more protruded-open position with the attached mandible. With this appliance design and tongue retention strap, the appliance is much more effective in treating more severe cases of obstructive sleep apnea than appliance prior designs.

Moreover, the mandibular advancement device can alleviate or treat Tempromandibular Joint Dysfunction (TMD) which may be related to bruxism/clenching, jaw muscle pain, TMJ ligament/disc problems and/or pre-existing TMJ arthritis among other potential causes, because use of the device reduces the mechanical loading of the jaw joints (TMJs) if the user grinds (bruxes) or clenches his/her teeth during sleep. It can also prevent the backward displacement of the mandible during sleep which allows compression of the neurovascular tissue located in the superio-posterior aspect of the TMJ fossa. In addition, the device can reduce/prevent muscle pain/spasms from overclosed jaws related to teeth/jaw clenching by establishing posterior contact between the maxillary and mandibular trays in an increased verticle (open) position, compared to the tooth to tooth contact during sleep of a bruxism and or TMD patient.

Retaining the tongue and mandible in a protrusive/open position during sleep also appears to reduce nocturnal jaw/tooth clenching and significantly reduce the amount of mechanical force related to jaw muscle contraction compared to a more posterior jaw position.

Various changes may be made in the invention without departing from the spirit and the scope thereof. It should be emphasized that the above-described embodiments of the present mandibular advancement device are merely possible examples of implementations and are merely set forth for a clear understanding of the principles of the invention. Many different embodiments of the mandibular advancement device described herein may be designed and/or fabricated without departing from the spirit and scope of the invention. All these and other such modifications and variations are intended to be included herein within the scope of this disclosure and protected by the following claims. Therefore the scope of the invention is not intended to be limited except as indicated in the appended claims.

What is claimed is:

1. A mandibular advancement device comprising:
   a maxillary appliance for receiving and retaining maxillary teeth;
   a mandibular appliance for receiving and retaining mandibular teeth; and
   at least two advancement prongs, located on said mandibular appliance in an anterior region thereof, wherein said advancement prongs, when in use, contact an outer surface of the maxillary appliance in an anterior region thereof, thereby advancing a wearer's mandible,
   said device further comprising
   a tongue strap in the form of a flexible elastic strap or a wire disposed between two most distal aspects of opposing portions of the mandibular appliance, wherein said flexible elastic strap or wire is configured to lie over a superior posterior or dorsal surface of the wearer's tongue when in use, wherein the tongue strap comprises a length of orthodontic elastic power chain or a flexible dental wire, and wherein the elastic power chain or flexible dental wire has a flexible tongue retaining pad that is connected between the opposing portions of the mandibular appliance by the elastic power chain or flexible dental wire.

2. The device of claim 1, wherein the advancement prongs comprise vertically extending projections.

3. The device of claim 1, wherein the mandibular appliance includes two raised occlusal bite pads in a region contiguous and posterior to the advancement prongs.

4. The device of claim 3, further comprising two additional raised occlusal bite pads located adjacent to the most posterior aspect of the mandibular appliance to prevent compression of the wearer's temporomandibular joint and shortening of the wearer's jaw closing muscles when the device is in use.

5. The device of claim 3, wherein an anterior lingual gap for passively retaining the wearer's tongue is formed between the advancement prongs and the occlusal bite pads of the mandibular advancement device when in use.

6. The device of claim 1, wherein the advancement prongs are coupled to the mandibular appliance at a region corresponding to near a distal aspect of the wearer's mandibular canines to near a distal aspect of the wearer's second premolars when in use.

7. The device of claim 1, wherein the maxillary appliance and the mandibular appliance are custom fabricated to precisely conform to the wearer's teeth.

8. The device of claim 1, wherein the tongue retaining pad includes a downwardly curved extension for engaging with a dorsal aspect of the wearer's tongue, retaining the tongue forward, yet allowing the tongue to move back during swallowing to produce a pharyngeal seal and avoid drooling, saliva buildup and regurgitation of stomach contents.

9. A mandibular advancement device comprising:
   a maxillary appliance for receiving maxillary teeth;
   a mandibular appliance for receiving mandibular teeth;
   at least two advancement prongs located on said mandibular appliance in an anterior region thereof, wherein said advancement prongs, when in use, contact outer surfaces of the maxillary appliance in an anterior region thereof, and wherein bite pads on said mandibular appliance adjacent to the at least two advancement prongs, when in use, contact occlusal surfaces of the maxillary appliance in an anterior region thereof, whereupon the device is advancing or retaining a wearer's mandible and opening a maxillary-mandibular space; and an elastic strap or a flexible orthodontic or dental wire disposed between two posterior portions of the mandibular appliance configured to lie over a superior posterior surface of the wearer's tongue when in use, wherein the elastic strap or flexible orthodontic or dental wire comprises a length of orthodontic elastic power chain or flexible orthodontic or dental wire, and a flexible tongue pad is connected between opposing right and left posterior portions of the mandibular appliance.

10. The device of claim 9, wherein the mandibular appliance includes two raised (bite pads in a region adjacent and posterior to the at least two advancement prongs.

11. The device of claim 9, wherein the mandibular appliance further includes two additional bite pads on the occlusal surfaces adjacent the most posterior aspects of the mandibular appliance.

12. The device of claim 11, wherein the two additional bite pads are in the form of vertical pads or blocks.

13. The device of claim 9, wherein a gap for passively retaining the wearer's tongue is formed, when in use, between the advancement prongs located in the anterior region of the device and in a space posterior to the advancement prongs.

14. The device of claim 9, wherein the advancement prongs are bonded to the mandibular appliance at a region corresponding to near a distal aspect of the wearer's mandibular canines to a distal aspect of the wearer's second premolars when the device is in use.

15. The device of claim 9, wherein the maxillary appliance and the mandibular appliance are custom fabricated to conform to the wearer's teeth.

16. The device of claim 9 wherein the flexible tongue retaining pad includes a downwardly curved extension for passively engaging with the dorsal aspect of the wearer's tongue.

* * * * *

UNITED STATES PATENT AND TRADEMARK OFFICE
CERTIFICATE OF CORRECTION

PATENT NO. : 8,881,733 B1  Page 1 of 1
APPLICATION NO. : 13/468766
DATED : November 11, 2014
INVENTOR(S) : Harkins It is certified that error appears in the above-identified patent and that said Letters Patent is hereby corrected as shown below:

In the Claims

Claim 10, Col. 8, line 36, "raised (bite" should be --raised bite--.
Claim 16, Col. 8, lines 56-57, "tongue retaining pad" should be --tongue pad--.

Signed and Sealed this
Seventeenth Day of February, 2015

Michelle K. Lee
*Deputy Director of the United States Patent and Trademark Office*